(12) United States Patent
Zobele et al.

(10) Patent No.: US 7,204,870 B2
(45) Date of Patent: Apr. 17, 2007

(54) DIFFUSER DEVICE FOR VOLATILE SUBSTANCES

(75) Inventors: Franco Zobele, Trento (IT); Fabio Marchetti, Povo (IT)

(73) Assignee: Zobele Holding SpA, Trento (IT)

( * ) Notice: Subject to any disclaimer, the term of this patent is extended or adjusted under 35 U.S.C. 154(b) by 408 days.

(21) Appl. No.: 10/941,683

(22) Filed: Sep. 15, 2004

(65) Prior Publication Data

US 2005/0218243 A1   Oct. 6, 2005

(30) Foreign Application Priority Data

Apr. 6, 2004   (IT) .......................... MI2004A0681

(51) Int. Cl.
*B01D 50/00* (2006.01)
(52) U.S. Cl. .......................... 96/222; 422/124; 261/30; 261/DIG. 88; 239/55; 239/58
(58) Field of Classification Search ................. 96/222; 261/30, DIG. 88; 422/124; 239/35, 55, 239/58, 59, 94; 392/394
See application file for complete search history.

(56) References Cited

U.S. PATENT DOCUMENTS

| | | | |
|---|---|---|---|
| 4,370,300 A | 1/1983 | Mori et al. ................. 422/108 |
| 5,735,918 A | 4/1998 | Barradas ....................... 55/274 |
| 6,254,065 B1 | 7/2001 | Ehrensperger et al. ........ 261/26 |
| 6,511,531 B1 | 1/2003 | Cartellone .................... 96/222 |
| 2005/0066818 A1* | 3/2005 | Kim ............................. 96/222 |

FOREIGN PATENT DOCUMENTS

EP    1 172 119 A2    1/2002

* cited by examiner

*Primary Examiner*—Robert Hopkins
(74) *Attorney, Agent, or Firm*—Merchant & Gould

(57) ABSTRACT

A diffuser device (1) for volatile substances comprises a motor unit (2) and a refill unit (3) which can be assembled with each other. The motor unit (2) comprises a fan (6) for sucking in air comprising a body (60) and an electric motor (M1) which drives a plurality of blades (62) in rotation, electrical power supply means (4, 5) for the motor (M1) and a structure (20, 21) to support the fan (6) and the power supply means (4, 5). The refill unit comprises a refill of volatile substances (9), air filtering means (90) and a support structure (30) for the refill (9) and the filtering means (90). The filtering means (90) are situated upstream of the fan (6) to filter all the air sucked in by the fan (6). A laminar air flow generated in the fan body (60) strikes the refill (90) to favour diffusion of the volatile substances.

18 Claims, 4 Drawing Sheets

DIFFUSER DEVICE FOR VOLATILE SUBSTANCES

The present invention refers to a device for diffusing volatile substances with filtered and purified air into an environment.

Solutions are already known to the art which allow simultaneous treatment of the air in an environment to be performed through filtering and subsequent freshening (U.S. Pat. No. 5,735,918 by G. Barradas, U.S. Pat. No. 4,597,781 by D. Spector).

In these systems a motor fan sucks in the air from the environment, passing it through filters that allow the noxious particles dispersed in the air as well as the unpleasant odours to be separated and trapped. The air is subsequently passed though a porous material impregnated with volatile substances, and thus enriched with these aromas. The fan system then ensures that the treated air is expelled and diffused into the environment.

Whilst in the system proposed by D. Spector all the filtered air is subsequently enriched with the aromatic elements, in the system proposed by G. Barradas perfuming takes place only on a part of the filtered air.

In both systems there is no clear indicator of the end of the product's life either as far as the filtering elements are concerned or as far as the elements containing the volatile products which perfume the air are concerned.

A further drawback in both of the proposed systems is the difficulty encountered by the final user in replacing the active elements of the device, that is the filtering elements and the elements containing the volatile products, since these are integrated into the device.

The system proposed by D. Spector has no regulation system that allows the content of volatile substances given out into the air by the device to be regulated.

In the system proposed by G. Barradas there is a regulation system which does not act on the amount of aromatic substance evaporated, but rather on the amount of aromatised air given out by the device.

Furthermore, in the system proposed by G. Barradas the filtering element is positioned behind the suction fan. In this manner, much of the dust contained in the air is deposited on the surface of the fan blades which, due to the continuous movement, develop a certain electrostatic charge. As the device operates, a build-up of dirt on the fan blades is therefore seen.

Also well known are various solutions of other devices which, without carrying out any filtering or decontaminating action on the air, allow specific substances to be released into the air.

In many of these cases evaporation of said products is favoured by the temperature. The heat provided by a heating element leads to an increase in the temperature of the surrounding air and thus to a heating of the surface of a material containing the specific product. This favours and accelerates the evaporation of the substance.

European patent application EP 1 252 899 by Falchieri describes a device for diffusing volatile substances, in which the thermal gradient that is established in the device between hot parts and cold parts allows the creation of a convective movement of the air (chimney effect), which helps to disperse the evaporated substance into the environment. The more efficient the chimney effect, the greater the dispersion of the substance into the environment.

However, in this case, the ability to diffuse the product at a distance from the diffuser is in any case limited and proves considerably dependent upon any systems for regulation of the rate of evaporation based on direct or indirect lowering of the temperature.

Regulation systems with direct lowering of the temperature entail a decrease in the working power of the device. On the other hand, those based on indirect lowering of the temperature entail moving the body containing the product away from the heat source, decreasing the evaporating surface or narrowing the air passage. All these temperature regulation systems also involve a decrease in the chimney effect of the system.

To overcome this and to maintain an adequate diffusion of the product into the environment, it has been proposed that the diffuser device be provided with a blade system like that described in U.S. patent application Ser. No. 2003/019435 by A. Pedrotti et al., which, however, has no effect on the product evaporation process. In this case a considerable limitation is represented by the size of the device and by the fact that only part of the air flow generated by the blade system is exploited for diffusion of the product into the environment. Furthermore, this diffusion system requires a liquid refill, thus it must operate with a precise orientation in order to avoid leakage of the liquid from the refill.

There also exist diffusion systems such as that described in EP 0 836 857, in which evaporation is favoured by a flow of air which passes through or sweeps over a porous material impregnated with a specific product. In this case, the diffusion of the product into the environment is ensured by the ventilation system, but an air filtering capacity is lacking and the regulation significantly penalises diffusion of the product into the environment.

Furthermore, a large proportion of the diffusion systems proposed, having to be battery operated, uses small brush motors which have a relatively short life and a rather high noise level.

Object of the present invention is to eliminate the drawbacks of the prior art by providing a diffuser device for volatile substances which at the same time allows filtering of the diffused air.

Another object of the present invention is to provide a diffuser device that is able to act on all the filtered air and at the same time it is able to carry out a fine regulation of the substances diffused.

Yet another object of the present invention is to provide a diffuser device that is able to provide information on the state of life of the filtering means and of the diffusing means and at the same time allows an easy replacement of said filtering means and of said diffusing means.

These objects are achieved in accordance with the invention with the characteristics listed in appended independent claim 1.

Advantageous embodiments of the invention are apparent from the dependent claims.

The diffuser device for volatile substances according to the invention comprises a motor unit that can be assembled with a refill unit.

The motor unit comprises an air suction fan comprising a body and an electric motor that drives a plurality of blades in rotation, electrical power supply means to power the fan motor electrically, and a support structure able to support the fan and the electrical power supply means.

The refill unit comprises a refill containing volatile substances to be diffused, filtering means for air filtering and a support structure able to support the refill and the filtering means.

The filtering means are disposed upstream of the fan to filter all the air sucked in by the fan.

The fan body has an air inlet aperture that allows an incoming flow of air along the axis of rotation of the fan blades and an outlet aperture disposed so as to allow a laminar outgoing air flow, substantially at right angles to the incoming air flow. The laminar outgoing air flow strikes the refill to favour diffusion of the volatile substances.

The diffuser device according to the invention simultaneously allows multiple treatment of the air in a particular environment. The air is sucked from the environment into the device by means of said fan, passing first through a filter which, thanks to its structure with different weaves and/or because of the electrostatic characteristics of the surface of its fibres, favours trapping and elimination of polluting factors such as dust, unpleasant odours, smoke, etc.

The air thus filtered, again by means of the same blade device, is subsequently forced along a particular channel where, sweeping the surface of the refill containing a specific product to be evaporated, it favours evaporation of said product.

The surface of the refill struck by the flow of air can be formed by a membrane permeable to the vapours of the product or by a porous element that is in contact with and is soaked with the liquid of the refill. In this manner the filtered air is enriched with specific products such as medicaments, decongestants, repellents, insecticides, bactericides, deodorants and the like and is released into the environment again through an outlet hole. The flow of air generated by the blade device ensures an adequate diffusion into the environment of the treated air enriched with specific substances.

By operating on the direction of flow of the air or on the relative position of the evaporating surface with respect to said air flow, it is possible to have a system for regulating the evaporating rate of the device, that is the amount of product diffused in a unit of time.

Operation of the diffuser device is conditioned by the presence of the refill body which also acts as the activator of the entire system. The diffuser device is further provided with an operating light which allows the device to be used also as a night light.

Further characteristics of the invention will be made clearer by the detailed description that follows, referring to a purely exemplary and therefore non-limiting embodiment thereof, illustrated in the appended drawings, in which:

FIG. 1 shows the diffuser device according to the invention in its entirety, denoted by reference numeral 1.

Figure 2:
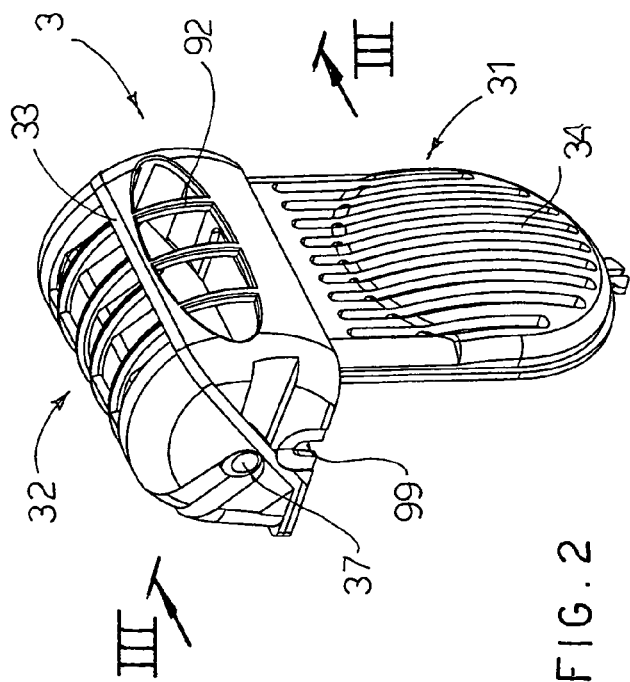
FIG. 2 is a perspective exploded view illustrating the two main units of the diffuser device of FIG. 1, that is to say the fan motor unit and the volatile substance refill unit.
Figure 2:
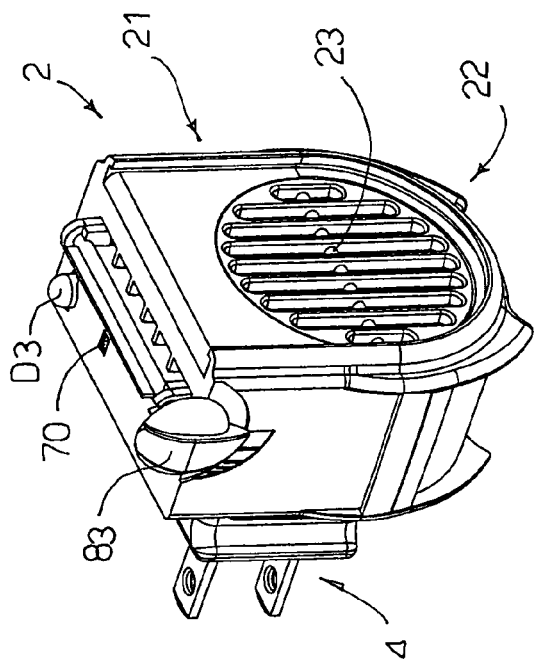
Figure 1:
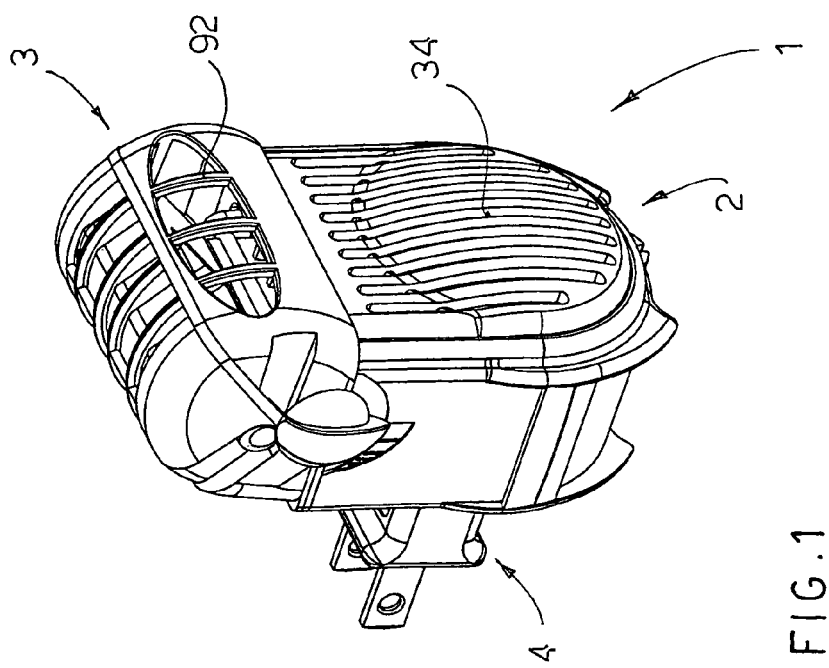
FIG. 1 is a perspective view illustrating the diffuser device for volatile substances according to the invention, in an assembled configuration.

As shown in FIG. 2, the diffuser device 1 comprises two main assemblies: a motor assembly 2 and a refill assembly 3.

Figure 4:
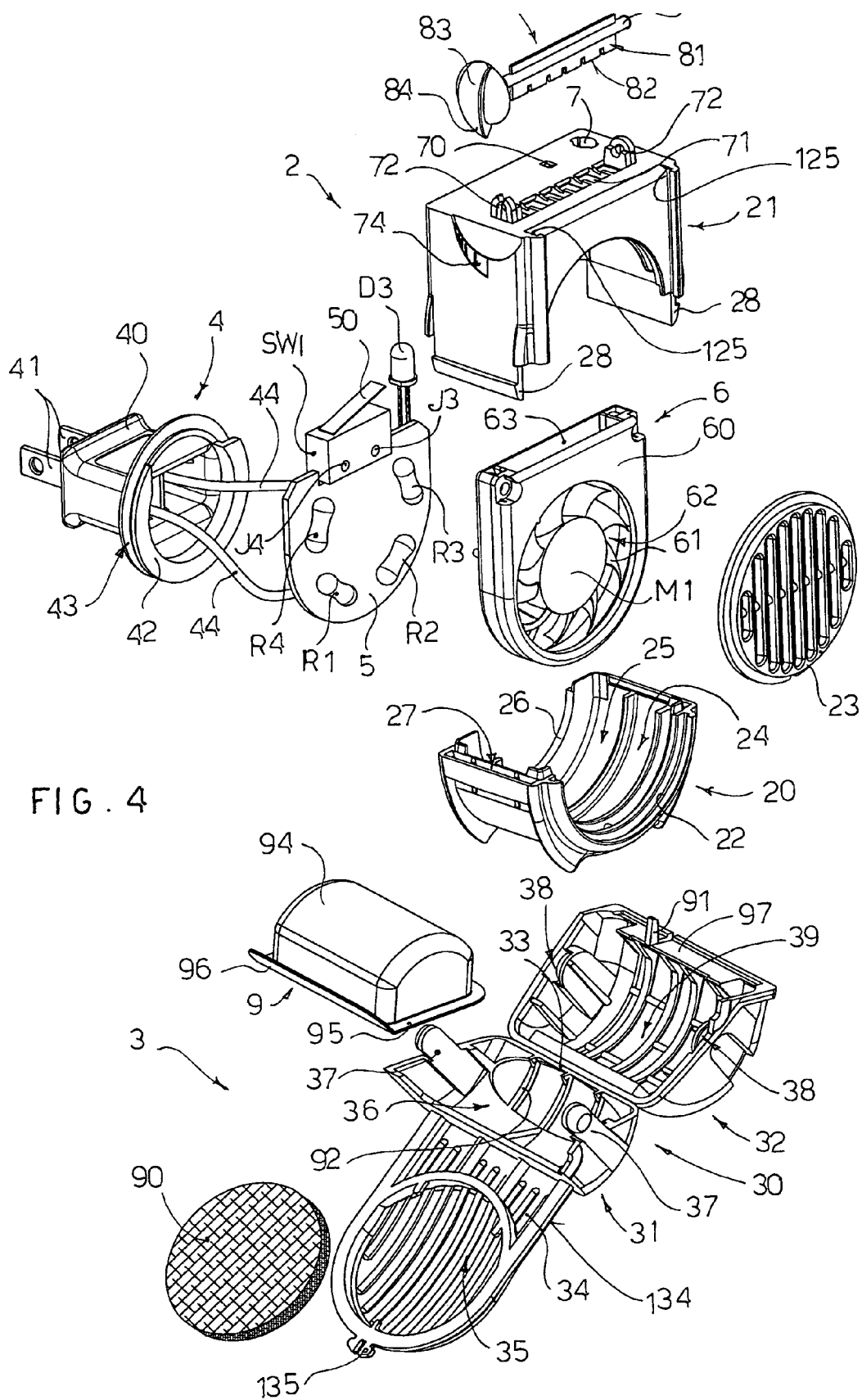
FIG. 4 is a perspective view, illustrating the various elements of the diffuser device of FIG. 1 exploded, in which the fan body is illustrated from the front.

As shown in FIG. 4, the motor assembly 2 comprises a fan 6 driven by a motor M1 of the brushless type. The motor M1 has a rotor which drives in rotation a plurality of blades 61. The rotor of the motor M1 is mounted rotatably in a fan body 60 shaped like a substantially flattened box with the bottom peripheral edge substantially curved.

A circular front aperture 62 having a large enough diameter to leave the blades 61 uncovered is provided in the front wall of the fan body 60. A rectangular top aperture 63 is provided in the top wall of the fan body 60. In this manner, when the blades 61 turn, driven by the motor M1, the air is sucked in by the front inlet aperture 62 and exits from the top outlet aperture 63.

The motor assembly 2 comprises an electric plug 4 which allows the diffuser device 1 to be connected to the electrical main. The electrical plug 4 comprises a plug body 40 wherefrom the male pins 41 protrude for insertion in an electrical socket of the electrical main. At the front of the plug body 40 there is provided a circular flange 42 which defines a peripheral annular seat 43.

The pins 41 of the plug are connected electrically, by means of electrical cables 44, to a printed circuit board 5 wherein the operating circuitry for the diffuser device 1 is integrated. The bottom edge of the board 5 is substantially curved.

Figure 6:
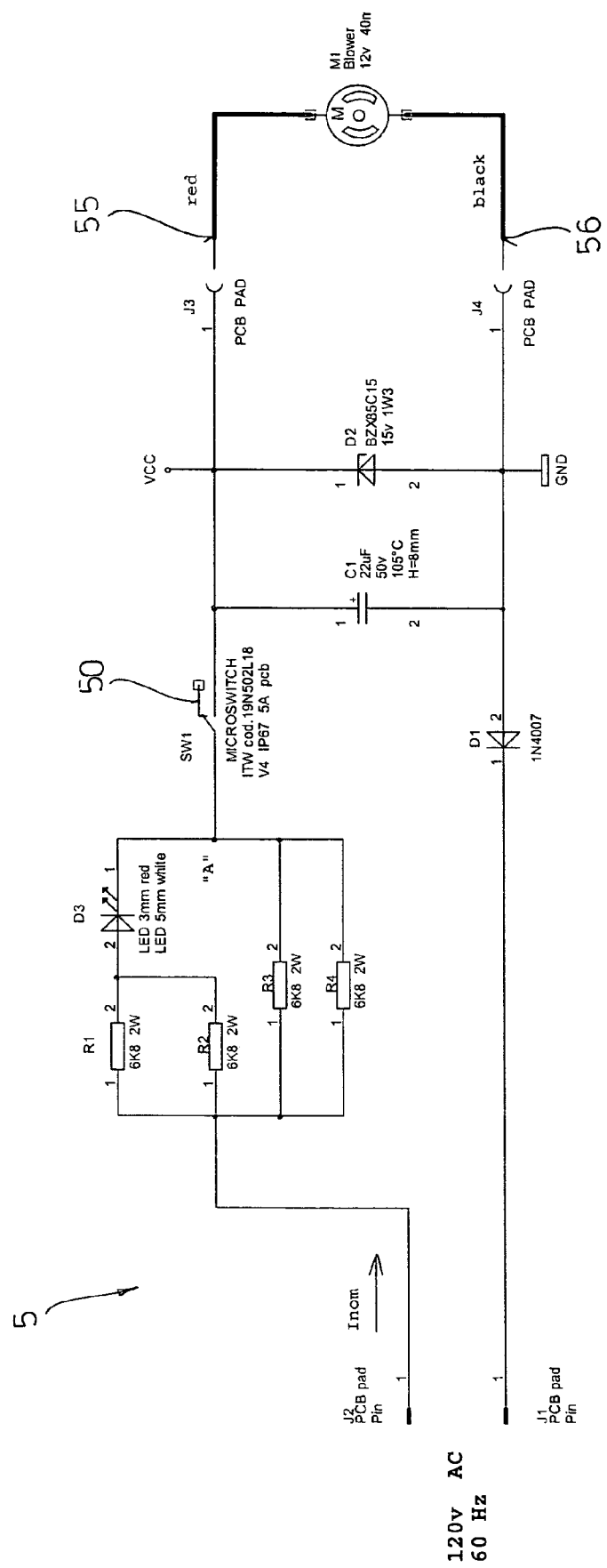
FIG. 6 is a wiring diagram of the motor operating circuit.

In FIG. 6 the circuitry of the circuit board 5 is illustrated. The board 5 comprises:
  two inlet pads J1 and J2 connected respectively to the electrical cables 44 of the plug, and
  two outlet pads J3 and J4 to be connected to electrical contacts of the motor M1 of the fan 6.

A resistor bridge consisting of four resistors R1, R2, R3 and R4 is connected to the supply pad J2. The resistor bridge is able to create a reduction in the alternating voltage coming from the electric main and to prepare a suitable current to supply to the motor M1. The resistor bridge comprises a first resistive branch (R1 in parallel with R2) and a second resistive branch (R3 in parallel with R4) connected to a LED D3 able to give out a light signal indicating operation of the diffuser device 1. A normally open switch SW1 is connected to the outlet of the resistor bridge and of the LED D3.

As shown in FIG. 4, the resistors R1, R2, R3 and R4 are disposed in the front surface of the circuit board 5. On the other hand the LED D3 and the switch SW1 are disposed on the top edge of the circuit board 5. The switch SW1 is controlled mechanically and is closed by pressing a lever 50 disposed in its top surface.

Returning to FIG. 6, and defining the supply voltage to the motor M1 as VCC, in the outlet stage of the circuit there are a Zener diode D2 able to fix the maximum supply voltage of the motor M1 and an electrolytic capacitor C1 in parallel with the Zener diode D2 to level and even out said output tension. Furthermore, the ground GND of the circuit is connected to the inlet pad J1 by means of a rectifying diode D1 which regulates the dissipated power of the resistor bridge R1–R4 and establishes the direction of rotation of the motor M1.

The windings of the motor M1 are connected to electrical cables 55 and 56, which are connected to the output pads J3 and J4 for the power supply to the electric motor M1.

Figure 5:
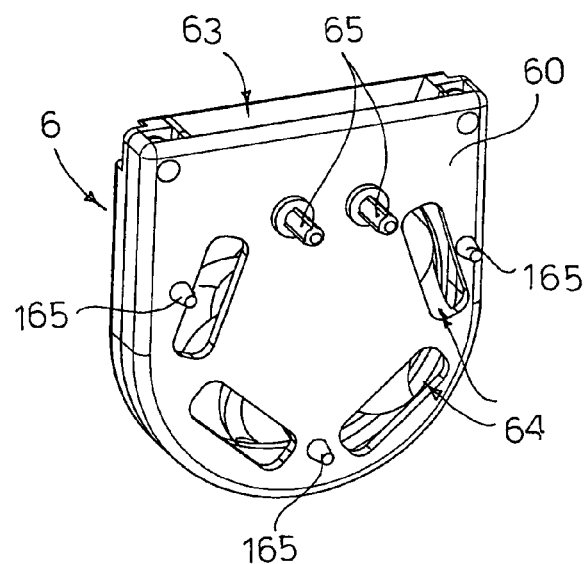
FIG. 5 is a perspective view illustrating the fan body from the rear.

As shown FIG. 5, four slots 64 able to accommodate the resistors R1, R2, R3 and R4 of the circuit board 5 are provided in the rear wall of the fan body. The resistors R1, R2, R3 and R4 are partially inserted in the body 60 of the fan 6. This arrangement allows the air sucked in by the fan blades 62 to be exploited for cooling the surface of said resistors, thus improving the thermal dissipation thereof and reducing damage thereto with operation.

Again in the rear wall of the fan body 60, structures or spacers (65, 165) are provided to keep the circuit board 5 at a distance from the fan body 60.

The motor assembly 2 further comprises a supporting and containing structure consisting of a bottom half-shell 20 and a top half-shell 21.

Figure 7:
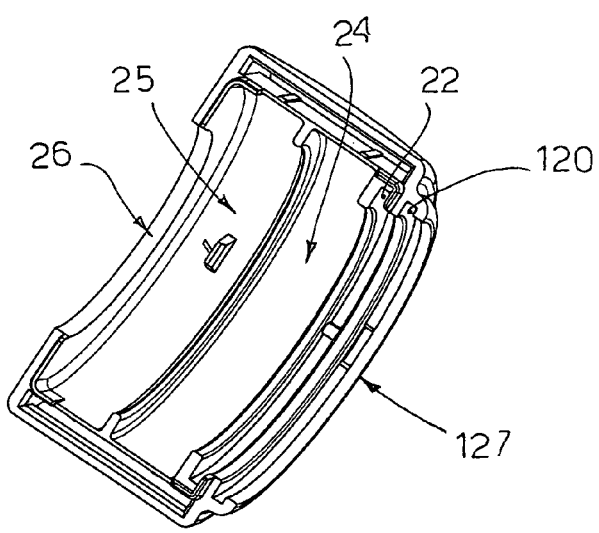
FIG. 7 is a perspective view of the bottom half-shell of the motor unit, but seen from a different angle with respect to FIG. 4.

As shown also in FIG. 7, the bottom half-shell 20 is substantially semi-cylindrical in shape and comprises, starting from its front part:
  a first seat 120 to receive a bottom edge (track) 134 of the bottom structure 31 of the refill body 3, a slot 121 formed in the first seat 120 to anchor the bottom structure 31 of the refill body 3 by means of a hook 135 present on the bottom peripheral edge of the bottom structure 31 of the refill body, a second seat 22 to receive the bottom peripheral edge of a front circular grille 23, a third seat 24 to receive the bottom edge of the fan body 60, a fourth seat 25 to receive the bottom edge of the circuit board 5, and a curved rear edge 26 able to engage rotatably in the curved seat 43 of the front flange 42 of the plug 4 to adjust the position of the plug 4 according to the orientation of the socket.

Two slots 27 are provided in the top side edges of the bottom half-shell 20.

The top half-shell 21 is shaped as a small parallelepiped block in the form of a bridge. The side walls of the top half-shell 21 have two flexible tongues 28 able to engage in a snap-in coupling relationship in the slots 27 of the bottom half-shell 20. Two seats 125 to receive the peripheral side edges 134 of the bottom structure 31 of the refill body are provided in the front part of the top half-shell 21.

In the top wall of the top half-shell 21 there are formed:

a first slot 7 able to accommodate the LED D3 of the circuit board 5, so that it can be seen from the outside, a second slot 70 in register with the lever 50 of the switch SW1 of the circuit board 5, and an array of slots 71 disposed in register with the top aperture 63 of the fan body 60.

At the ends of the array of slots 71 there are two support brackets 72 able to receive rotatably the ends of a shaft 80 of a deflector-type regulation device 8. Integral with the shaft 80 of the regulation device there is a plate 81 having a plurality of tongues 82 designed to engage with a certain slack in the respective slots 71 of the array of slots. The tongues 82 serve as shutters for the slots 71.

A knob 83 which has an indicator 84 which points to a graduated scale 74 realised on a side wall of the top half-shell 21 is integral with one end of the shaft 80. The graduated scale 74 indicates the amount of volatile substances diffused by the diffuser device 1, according to the regulation performed.

In this manner, by manually turning the regulation device 8 by means of the knob 83, according to the inclination of the tongues 82 the aperture of the slots 71 is increased or decreased and thus the direction of flow of the air coming from the aperture 63 of the fan 6 is modified.

The refill unit 3 comprises:

the refill 9, in the form of a reservoir containing a liquid wherein the volatile substances to be diffused are dispersed, a filter or a set of filters 90 to filter the particles in the air, and a support structure 30 to contain the refill 9 and the filter 90.

The support structure 30 comprises a bottom portion 31 hinged to a top portion 32 along a hinging line 33 so that it can be shut like a book.

The top portion 32 has a concave housing 39 designed to accommodate the refill 9. The bottom part 31 has a chamber 36 comprising a slot 92 to allow the air to exit to the outside. Furthermore, in the bottom portion 31 there are two retaining tongues 37 able to engage in a snap coupling relationship inside respective seats 38 formed in the housing 39 of the top portion 32.

In the top portion 32, on the end edge opposite the hinge 33 an abutment surface 97 is provided from which protrudes a pin 91 able to engage in the hole 70 of the top half-shell 21 so as to operate the lever 50 which closes the switch SW1 of the circuit board 5.

Figure 3:
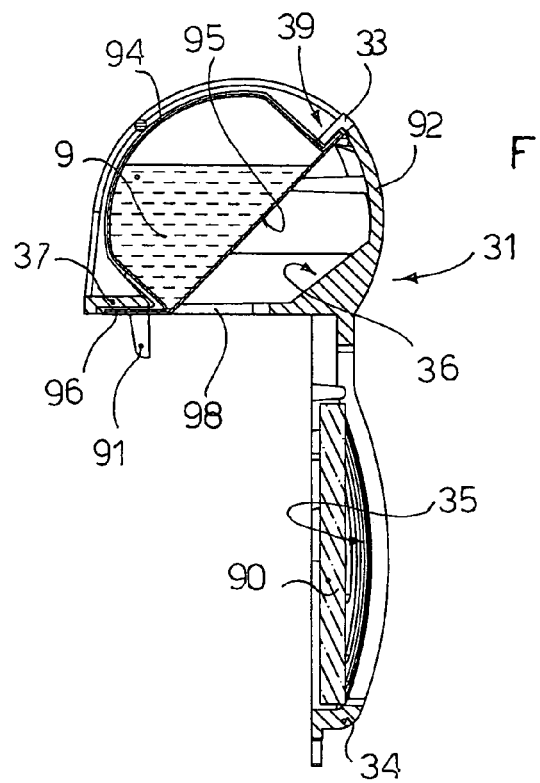
FIG. 3 is a cross section of the refill unit, taken along the plane of section III—III of FIG. 2.

The refill 9 has a curved top wall 94 and a flat bottom wall 95 provided with an inclined flap 96. The refill 9 is inserted in the top housing 39 (FIG. 3) so that the flap 96 abuts against the abutment surface 97 of the top housing 39 and the top wall 94 of the refill abuts on the inside surface of the housing 39 of the top portion 32. The flat bottom wall 95 of the refill 9, on the other hand, faces towards the grille 92 of the chamber 36 of the bottom portion 31.

When the structure 30 is closed (FIG. 3) the refill 9 is housed in the top housing 39 and the bottom surface 95 of the refill is disposed obliquely facing towards the bottom housing 36. It should be noted that an aperture 98 for the passage of air is provided in the bottom wall of the bottom chamber 36. In this manner a channel is created for the air which enters through the aperture 98 and exits through the slot 92, sweeping the flat bottom wall 95 of the refill.

The bottom surface 95 of the refill 9 is positioned with an inclination of about 45° with respect to the plane of the aperture 98 for entry of the air sucked in by the fan 6. In this manner, the vertical air flow which enters the aperture 98 strikes the bottom surface 95 of the refill with an optimal angle of incidence to generate a laminar effect and to increase the efficiency of evaporation of the product. By changing the inclination of the deflector device 8, the direction of flow of the incoming air is changed and thus the conditions of evaporation of the system are changed.

The refill 9 is made of impermeable material and is closed by its bottom surface 95 which represents the evaporation surface for the product contained in the reservoir. The bottom surface 95 of the refill can be formed by a membrane permeable to the vapours of the product or by a porous element that remains impregnated with the product. Before use, said bottom surface 95 is protected with a peelable impermeable film. Said film is removed when the refill 9 is positioned inside its housing 39.

Of course, in place of the refill 9 with liquid products, gel products or products in a solid state contained directly in the housing 39 of the refill body can be provided.

The material used for the refill 9 is transparent. In this manner the user can see how much liquid is still present in the refill 9 or if said liquid is finished, indicating the end of the product's life.

The bottom portion 31 comprises:

a peripheral edge in the form of a track 134 which allows it to be fixed slidably in the specific seats (120, 125) of the bottom half-shell 20 and of the top half-shell 21 of the body 2;

a spring hook 135 disposed in the bottom end and destined to engage in the slot 121 of the bottom half-shell 20 to allow the refill body 3 to be secured to the motor body 2, and a flattened grille part 34 which protrudes downward.

A circular seat 35 able to receive the filtering means 90 which are disc-shaped is formed in the inner surface of the grille part 34. When the diffuser device 1 is assembled, the grille part 34 is disposed in front of the grille 23 of the motor body 2.

The filtering element 90 has a fibrous "woven" structure able to obtain a mechanical action of retaining the dust particles contaminating the air. Furthermore, because of the mechanical rubbing action related to the continuous passage of air sucked in by the movement of the fan blades 62, an electrostatic charge able to attract and to retain the particles that pass through the filter develops on the surface of the fibres of the filter 90. The filter 90 preferably comprises a sequence of filtering elements with a different "mesh" to block dust particles of very small size.

The filtering and purifying function of the filter 90 can be enriched by choosing filtering elements made up of specific materials, such as polyester-based reticulated polyurethane foams, with a complementary open cell structure. The calibrated, complementary open cell structure ensures a reproducible filtering efficiency, whilst the three-dimensional structure allows high dust retention without significantly affecting the pressure drop through the filtering element 90.

A further factor to increase the functionality of the filtering element could be to treat the surface of the fibres making up the filter with specific products, so as to exert a chemical action that facilitates the trapping of unpleasant odours and of smoke present in the air sucked in.

Furthermore, the filter 90 is made with materials in light colours which, due to the filtering action, change colour as they become "dirty" and provide an easy, simple indication that the filter is exhausted.

It should be noted that so long as the refill body 3 is separated from the motor body 2, the switch SW1 remains open. Thus both the fan 6 and the light signal D3 are not powered even if the plug 4 is connected to the electrical main.

When the refill body 3 is coupled to the motor body 2 which is connected to the electrical main, the pin 91 of the refill body 3 operates the lever 50 of the switch SW1 and both the fan 6 and the signal light D3 are powered.

The air is sucked in by the fan 6 along the horizontal axis of rotation of the blades 62. On striking the rear wall of the fan body 60, the horizontal air flow is transformed into a vertical air flow which passes though the top opening 63 of the fan body. The vertical air flow exiting through the top aperture of the fan body passes through the array of slots 71 of the regulation device 8 and the bottom aperture 98 of the bottom part 31 of the refill body. Thus the vertical air flow strikes the bottom wall 95 of the refill, which is disposed inclined, and is transformed into a laminar flow which is expelled to the outside through the apertures of the grille 92 of the refill body.

As a result, a laminar air flow is created at right angles to the direction of the air sucked in. Said laminar flow strikes the bottom surface 95 of the refill 31 generating a further laminar air flow which exits from the diffuser device 1 through the grille 92. It should be noted that the air, through said laminar flow, favours evaporation of the substances present on the bottom surface 95 of the refill without the need to introduce specific elements, such as localised heating.

In addition, by exploiting the heat dissipation of the resistors R1, R2, R3 and R4 and the capacity of the fan system 6 to remove said heat generated by the resistors, the air moved by the fan 6 is heated and thus further favours the phenomenon of evaporation of the product from the bottom surface 95 of the refill.

Another important aspect to be underlined is the fact that by moving the air with the fan 6, diffusion into the outside environment of the volatile product contained in the refill 9 is favoured, preventing the volatile product from remaining localised only near the diffuser device 1.

The diffuser device 1 can have an ioniser (per se known and therefore not shown) disposed downstream of the fan 6. In this manner the air, before being enriched with particular substances and introduced into the environment, could also be ionised, favouring the creation of negative ions which are particularly important in order to have a healthier environment.

The diffuser device 1 is designed to ensure a regulation of the amount of volatile product to be introduced into the environment. Said regulation can be achieved by means of a shutter regulation device 8, changing the direction of flow of the air and thus reducing/increasing the amount of air forced into the air passage channel toward the outside.

In addition to or instead of the regulation device 8, a second regulation device (not illustrated), able to change the exposed surface of the permeable wall 95 of the refill 9 in contact with the air flow drawn by the fan 6, can be provided. In this case a screen can be provided in front of the permeable wall 95 of the refill that is operated manually by the user to vary the exposed surface of the permeable wall 95 of the refill 9.

If the device operates in very dark environments or at night, the light signal D3 also acts as a night light or as a position light. For this purpose, the top part 32 of the refill body 3 must be transparent to the light coming from the signal light D3 or alternatively the signal light D3 must not be covered by the refill body 3.

The evaporation system according to the invention has the following advantages.

The particular support structure 30 of the refill unit 3 containing the various functional elements (the filters 90 and the refill 9) disposed so as to be easily replaceable makes it possible to obtain an extremely versatile device with small dimensions, operating in any position and orientation and aesthetically pleasing.

The provision of a brushless motor M1 to operate the fan 6 of the diffuser device ensures a very long running time and a considerable level of quietness (noiselessness during operation).

The system of filters 90 disposed in front of the fan allows all the air sucked in by the fan to be purified, capturing the particles present in the air mechanically, chemically or by means of an electrostatic charge. Said filters 90 also allow unpleasant odours present in the air to be reduced and removed. The colour of the new filters is advantageously white. As they are exhausted, becoming "dirty" with the captured particles, they change colour, thus providing a simple indicator of the end of the filtering system's life.

The refill 9 enriches the filtered air with specific products such as medicaments, decongestants, repellents, insecticides, bactericides, deodorants and the like. It serves as a reservoir where the product to be evaporated is stored and thus allows prolonged action over time. The refill is advantageously made of transparent material so as to easily verify when the product to be evaporated has been used up, thus providing a simple indication of the end of the life of the product.

The deflector regulation system 8 ensures a regulation of the amount of substances evaporated in the unit of time and thus of the content of volatile elements diffused by the device. Said deflector 8 changes the direction of the flow of the air generated by the fan 6, thus the amount of air that sweeps the permeable surface 95 of the refill increases and/or decreases, regulating the amount of product evaporated.

The thrust action of the fan 6 ensures that the air—purified, filtered and subsequently enriched with specific volatile substances—is re-introduced into the environment through the outlet aperture grille 92 and is diffused evenly and well away from the diffuser device 1.

The diffuser device 1 according to the invention works only when assembled, that is when the structure 30 containing the filter and the refill is inserted and coupled to the structure (20, 21) of the motor unit 3. In fact the pin 91 of the support structure 30 activates the switch SW1 for operation of the fan motor M1.

Operation of the diffuser device is signalled by a signal light D3 which, during possible night-time operation, also acts as a night light or signal light signals.

Numerous changes and modifications of detail within the reach of a person skilled in the art can be made to the present invention, without thereby departing from the scope of the invention as set forth in the appended claims.

The invention claimed is:

1. A diffuser device for volatile substances, comprising:
   a motor unit (2) comprising an air suction fan (6) comprising a body (60) and an electric motor (M1) that drives a plurality of blades (62) in rotation, electrical power supply means (4, 5) to power said fan motor (M1) electrically and a support structure (20, 21) able to support said fan (6) and said electrical supply means (4, 5); and
   a refill unit (3) comprising a refill (9) containing volatile substances to be diffused, filtering means (90) for air filtering and a support structure (30) able to support said refill (9) and said filtering means (90), characterised in that
   said refill unit (3) can be assembled on said motor unit (2) so that the filtering means (90) are situated upstream of said fan (6) to filter all the air sucked in by the fan (6); and
   said fan body (60) has an air inlet aperture (62) which allows an incoming flow of air along the axis of rotation of the blades (61) of the fan (6) and an air outlet aperture (63) disposed so as to allow a laminar outgoing flow of air, substantially at right angles to the incoming flow of air, wherein said outgoing flow of air strikes the refill (9) to favour diffusion of the volatile substances.

2. A diffuser device according to claim 1, characterised in that said refill (9) has a flat permeable surface (95) disposed substantially obliquely to the incident laminar flow of air coming from the outlet (63) of said fan, so as to generate a further laminar outgoing flow of air towards the outside environment.

3. A diffuser device according to claim 1, characterised in that it comprises regulation means (8) for regulating the amount of substances diffused, able to regulate the amount of air exiting through said outlet aperture (63) of the fan and incident on said refill (9).

4. A diffuser device according to claim 3, characterised in that said regulation means (8) comprise deflector/shutter means (82) able to regulate the air outlet size of an array of slots (71) formed in said support structure (21) of the motor unit in register with the air outlet aperture (63) of the fan (6).

5. A diffuser device according to claim 3, characterised in that said regulation means (8) comprise a knob (83) that can be operated by the user, having an indicator (84) which points to a graduated scale (74) realised on said support structure (21) of the motor unit.

6. A diffuser device according to claim 1, characterised in that it comprises means for regulating the amount of substances diffused, able to regulate the surface of a permeable wall (95) of said refill (9) exposed to the flow of incident air.

7. A diffuser device according to claim 1, characterised in that said electric motor (M1) of the fan is a direct current brushless motor.

8. A diffuser device according to claim 1, characterised in that said electrical supply means (4, 5) comprise an electric plug (4) designed to be connected to the electrical main and a printed circuit board (5) connected electrically to said electric plug (4) and electrically coupleable to said fan motor (M1).

9. A diffuser device according to claim 8, characterised in that a resistor bridge (R1, R2, R3, R4), able to create a reduction in the alternating voltage coming from the electrical main and to prepare a suitable current for the power supply of said motor (M1), is mounted in said printed circuit board (5).

10. A diffuser device according to claim 9, characterised in that said resistors (R1, R2, R3, R4) of the bridge of the circuit board (5) are inserted in respective slots (64) in the fan body (60) to be cooled by the air sucked in by the fan and to allow a flow of hot air incident on the refill (9).

11. A diffuser device according to claim 8, characterised in that in said circuit board (5) pads (J3, J4) able to go into electrical contact with electrical cables (55, 56) of said electric motor (M1) are provided.

12. A diffuser device according to claim 8, characterised in that in said circuit board (5) there is mounted an electric switch (SW1) able to open/close the supply circuit of said electric motor (M1).

13. A diffuser device according to claim 12, characterised in that said electric switch comprises an operating lever (50) which is operated when the refill unit (3) is mounted on the motor unit (2) so as to close the supply circuit of said motor (M1).

14. A diffuser device according to claim 8, characterised in that in said circuit board (5) there is mounted a light device (D3) able to emit a light signal indicating operation of said diffuser device and acting as night light device.

15. A diffuser device according to claim 1, characterised in that said filtering means (90) are made from light-coloured materials which, becoming dirty due to the filtering action, change their colour providing a simple indication that the filter is exhausted.

16. A diffuser device according to claim 1, characterised in that the reservoir of said refill (9) is made of a transparent material which allows the volatile substance contained therein to be seen, providing a simple indication that the refill is exhausted.

17. A diffuser device according to claim 1, characterised in that said support structure (30) of the refill unit comprises a book-type closing system consisting of a top part (32) in which the refill (9) is housed, hinged by means of a hinge (33) to a bottom part (31) which has a grille aperture (92) for the air to exit to the outside.

18. A diffuser device according to claim 1, characterised in that said support structure of the motor unit comprises a bottom half-shell (22) which houses said fan (6), said supply means (4) and a top half-shell (21) which is snap coupled on said bottom half-shell (20).

* * * * *